United States Patent [19]
Lin et al.

[11] Patent Number: 5,776,785
[45] Date of Patent: Jul. 7, 1998

[54] METHOD AND APPARATUS FOR IMMUNOASSAY USING FLUORESCENT INDUCED SURFACE PLASMA EMISSION

[75] Inventors: Jinn-nan Lin, Cerritos; Christopher J. Wilson, Redondo Beach, both of Calif.

[73] Assignee: Diagnostic Products Corporation, Los Angeles, Calif.

[21] Appl. No.: 777,406

[22] Filed: Dec. 30, 1996

[51] Int. Cl.$^6$ ............................................. G01N 33/552
[52] U.S. Cl. ........................... 436/527; 435/6; 435/7.1; 435/7.4; 435/7.9.2; 435/7.93; 435/7.94; 435/7.95; 435/962; 436/518; 436/524; 436/528; 436/531; 436/807
[58] Field of Search ..................... 356/445; 422/68.1, 422/82.05, 82.07, 82.08, 82.11; 435/6, 7.1, 7.4, 7.92, 7.93, 7.94, 7.95, 962; 436/518, 524, 527, 528, 531, 807

[56] References Cited

U.S. PATENT DOCUMENTS

| | | | |
|---|---|---|---|
| Re. 33,064 | 9/1989 | Carter et al. | 436/34 |
| 4,582,809 | 4/1986 | Block et al. | 436/527 |
| 4,649,280 | 3/1987 | Holland et al. | 250/483.1 |
| 4,775,637 | 10/1988 | Sutherland et al. | 436/527 |
| 4,810,658 | 3/1989 | Shanks et al. | 436/172 |
| 4,880,752 | 11/1989 | Keck et al. | 435/7.1 |
| 4,882,288 | 11/1989 | North et al. | 436/525 |
| 5,061,857 | 10/1991 | Thompson et al. | 250/458.1 |
| 5,064,619 | 11/1991 | Finlan | 422/82.05 |
| 5,340,715 | 8/1994 | Slovacek et al. | 435/6 |
| 5,344,784 | 9/1994 | Attridge et al. | 436/518 |
| 5,449,918 | 9/1995 | Krull et al. | 250/458.1 |
| 5,478,755 | 12/1995 | Attridge et al. | 436/518 |

FOREIGN PATENT DOCUMENTS

| | | |
|---|---|---|
| 0 170 376 | 2/1986 | European Pat. Off. . |
| 0 257 955 | 3/1988 | European Pat. Off. . |
| 0276142 | 7/1988 | European Pat. Off. . |
| 0 305 109 | 3/1989 | European Pat. Off. . |
| 0 346 016 | 12/1989 | European Pat. Off. . |
| 0 382832 | 8/1990 | European Pat. Off. . |
| 88/07202 | 9/1988 | WIPO . |
| 90/01166 | 2/1990 | WIPO . |

OTHER PUBLICATIONS

Weber et al., "Energy transfer from an excited dye molecule to the surface plasmons of an adjacent metal," Optics Letters, 4(8): 236–238, Aug. 1979.
Benner et al., "Angular Emission Profilers of Dye Molecules Excited by Surface Plasmon Waves at a Metal Surface," Optics Commonication, 30(2): 145–149, Aug. 1979.
Olney et al. "Optical effects of surface plasma waves with damping in metallic thin films," Applied Optics, 26(11): 2279–2282, Jun. 1987.

*Primary Examiner*—Carol A. Spiegel
*Attorney, Agent, or Firm*—Joseph E. Mueth

[57] ABSTRACT

A method and apparatus for immunoassays utilizes an improved collection technique of fluorescence induced emissions at the solid phase/liquid phase interface from surface plasmon resonance sensing devices. In a preferred embodiment, a solid phase substrate is coated with a thin film of a conducting material on which a first specific binding partner is directly or indirectly immobilized. The coated solid phase substrate is incubated with a liquid component comprised of a biological sample containing a specific ligand or analyte and a fluorescent labeled second specific binding partner in the case of immunometric assays, or a fluorescent labeled ligand or analog thereof in the case of competitive assays. The improvements in the method of light collection for the induced emission of surface plasmon resonance based sensing devices which involve
(a) irradiating the film of the stratified optical system from the substrate side with light that has a wavelength, polarization and angle of incidence appropriate for exciting surface plasmon resonance fluorescence;
(b) incubating the sample containing fluorescently labeled molecules with said solid phase substrate film; and
(c) employing 360° azimuthal collection of the fluorescence induced emission cone, and monitoring and analyzing the rate or amount by which the detected induced emission intensity changes as binding between the fluorescent or fluorescently labeled molecules and the film progresses.

27 Claims, 10 Drawing Sheets

METHOD AND APPARATUS FOR IMMUNOASSAY USING FLUORESCENT INDUCED SURFACE PLASMA EMISSION

BACKGROUND OF THE INVENTION

This invention relates to techniques for collecting radiation from sensing devices based on the phenomenon of surface plasmon resonance and means for improving such techniques. It further relates to the application of such techniques to qualitative and/or quantitative detection of chemical or biochemical analytes in a sample. In particular, the invention relates to techniques for improving assay sensitivity to chemical or biochemical analytes and to apparatus required for putting such techniques into effect.

The assay techniques utilized in the present invention exploit the affinity between the analyte to be assayed (hereinafter called "ligand") and a substance that binds specifically to the ligand (hereinafter called "specific binding partner"). Immunoassays based on antigen/antibody affinity interactions provide a common example. Such techniques are well known in the art and can be classified into two categories: (1) heterogeneous assays in which a physical separation of free from bound analyte is required, typically to separate free ligand and/or specific binding partner from that which is bound to the surface of a solid-phase, and (2) homogeneous assays in which no physical wash is required. In most cases, homogeneous assays provide lower sensitivity but require less time to perform when compared with heterogeneous assays. Both classifications require a detection method by which interactions between the ligand and the specific binding partner can be monitored.

A variety of sensing techniques exist, but of particular note for the present application are those that utilize evanescent waves to detect immunochemical interaction between a ligand and its specific binding partner. In such techniques the interaction typically occurs on the surface of a solid-phase containing ligand and/or specific binding partner. Since evanescent waves only detect near-surface interactions, the separation between free ligand and/or specific binding partner from that which is bound to the surface is achieved optically. This contrasts the physical separation of free from bound analyte required in heterogeneous assays. It also highlights a motivating goal behind many previously described evanescent wave techniques: to attain the sensitivity of a heterogeneous assay with a time efficient homogeneous assay. A number of such techniques have been disclosed.

Early examples include techniques employing total internal reflection (TIR) to detect changes in interaction dependent fluorescent intensity at the surface of a fiber optic waveguide (U.S. Pat. Nos. 4,582,809, 5,061,857, 4,880,752 and 5,340,715) or a planar waveguide (U.S. Pat. Nos. 4,775,637 and 4,810,658, EP-A-0170376, U.S. Pat. Nos. Re. 33064, 5,344,784 and 4,649,280). In these techniques, either the ligand or the specific binding partner is labeled with a fluorescent material. The waveguide serves as the solid-phase. Excitation light propagating within the waveguides undergoes multiple total internal reflections, thereby generating evanescent waves that extend a small distance into the liquid-phase from the solid-phase surface. The fluorescent label of any ligand or specific binding partner bound to the surface will be excited by the evanescent waves and emit light of a frequency different than that of the excitation light. The amount or rate of change of fluorescent emission due to ligand/specific binding partner interaction at the surface is analyzed to determine ligand concentration. Although these early techniques might offer improved sensitivity compared to conventional homogeneous assays, sensitivity is still inferior to that of heterogeneous assays and insufficient to measure especially low analyte concentrations.

Improved assay techniques have been disclosed in recent years that employ surface plasmon resonance to generate evanescent waves near the surface of diffraction gratings (WO-A-88/07202, U.S. Pat. No. 4,882,288, EP-A-0346016, EP-A-0257955, EP-BI-0276142, and U.S. Pat. No. 5,449, 918). A thin metal film is coated onto one side of the grating with said metal film to serve as the solid-phase. Excitation light at a predetermined angle of incidence is reflected from the grating side of the metal film, thereby generating an evanescent wave that extends a small distance into the liquid-phase from the opposite side of the metal film. The ligand/specific binding partner interaction is detected by one of two methods, depending on the technique and embodiment employed. One method involves analyzing changes in the properties of the reflected excitation light resulting from alteration of the evanescent wave due to complex formation on the solid phase surface. The other method involves analysis of the properties of an emission induced by a fluorescent substance that is used to label the ligand, used to label the specific binding partner, or immobilized on the solid-phase surface. The latter method provides an example of a class of evanescent wave techniques whose heretofore described detection mechanism is referred to as surface plasmon resonance fluorescence (SPRF). These techniques include a means for collection of the fluorescence induced emission that involves positioning a light detection device in the path of the emission light within the plane of incidence of the excitation light. The small angular separation between the path of the reflected excitation light and that of the emission light within the plane of incidence results in a high background signal from the light detection device and low signal-to-noise ratio. Consequently, assay sensitivity for these techniques is still inferior to most conventional heterogeneous assays.

Several types of surface plasmon resonance fluorescence based assay techniques are disclosed in EP-BI-0382832, U.S. Pat. No. 5,478,755 and WO-90/01166. Collection of the fluorescence induced emission is achieved by positioning a light detection device in the path of the emission light within a plane substantially at right angles to the plane of incidence of the excitation light. In such an arrangement, background signal due to excitation light is reduced. Further disclosed is a technique and means by which a specific type of surface plasmon resonance, referred to as long-range surface plasmon resonance (LRSPR), can be utilized to achieve an increase in the ratio of the field intensity of the evanescent wave at the solid-phase/liquid-phase interface to that of the excitation light at the surface of incidence (said ratio hereinafter referred to as "interfacial enhancement"). The increase in interfacial enhancement is described as resulting in a corresponding increase in the intensity of the fluorescence induced emission relative to that of the excitation light at the surface of incidence by a factor of 10 as compared with conventional surface plasmon resonance fluorescence. The disadvantages of this procedure are two with regard to constructing a practical device for performing assays. First, the range within which the angle of incidence of the excitation light must fall is roughly an order of magnitude narrower than the 0.5 degree range of conventional surface plasmon resonance. Such a level of precision is difficult to achieve in an instrument to be manufactured on a production scale. Second, typical metal film thicknesses required are very thin, e.g., 15.5 nm being disclosed for silver as compared with 54 nm for conventional surface plasmon resonance (Olney, R. D. and Romagnoli, R. J., Applied Optics 26:2279 (1987)). Even using state-of-the-art thin-film coating technology, manufacturing such a film reproducibly on a production scale is a challenging task.

SUMMARY OF THE INVENTION

One object of the present invention is to improve collection of fluorescence induced emissions from sensing devices that utilize the phenomenon of surface plasmon resonance. In so doing, the capability of performing an assay with the convenience of a conventional homogeneous assay and sensitivity to ligand concentration comparable to or better than conventional heterogeneous assays is realized.

Briefly, this invention includes an immunoassay method for the qualitative and/or quantitative detection of chemical or biological analytes in body fluids which comprises (a) a pre-formed solid phase substrate coated with a thin film of a conducting material appropriate for supporting surface plasma waves on which a first specific binding partner is directly or indirectly immobilized; (b) a liquid component comprised of a biological sample containing a specific ligand or analyte and a fluorescent labeled specific binding partner in case of immunometric assays, or a fluorescent labeled ligand or analog thereof in the case of competitive assays; (c) irradiating the film of the stratified optical system from the substrate side with light that has a wavelength, polarization and angle of incidence appropriate for exciting surface plasmon resonance fluorescence; (d) incubating the sample containing fluorescent or fluorescently labeled molecules from (b) with said solid phase substrate film from (a); (e) employing at least about 360° azimuthal collection of the fluorescence induced emission cone- and (f) measuring the rate or amount by which the detected induced emission intensity changes as the binding between the fluorescently labeled molecules and the film progresses which is directly or indirectly proportional to the amount of analyte present in the sample.

The invention also comprehends an apparatus for fluorescence immunoassays comprising: (a) a pre-formed solid phase substrate coated with a thin film of a conducting material appropriate for supporting surface plasma waves in contact with fluorescently labeled molecules; (b) a light source arranged so that it can excite the surface plasmon fluorescence induced emission by irradiating the film of the stratified optical system from the substrate side with an appropriate wavelength, polarization and angle of incidence; and (c) a collection optics and a photodetector arranged such that at least about 360° azimuthal collection of the fluorescence induced emission cone is achieved.

According to a preferred embodiment of the present invention, a substrate is coated with a thin film on which specific binding partner is directly or indirectly immobilized. The film may be comprised of one or more layers, at least one of which must be a conducting material. A beam of light entering the substrate impinges on the substrate/film interface at a suitable angle or range of angles to excite surface plasma waves (SPWs) via total internal reflection. Surface plasma waves having associated with them evanescent waves which propagate along the film/sample interface and decay exponentially in amplitude in the direction perpendicular to the interface. Since the amplitude of the evanescent field exceeds that of the incident field by a factor of 10 to 100 times depending on the materials used for the optical element, the evanescent field enhances the emission from fluorescently labeled ligand bound to the film surface.

The fluorescent label emits evanescent waves which generate surface plasma waves at the fluorescence emission frequency. These, in turn, radiate propagating waves (hereinafter called "induced emission") through the film and into the substrate that are confined to a narrow range of angles relative to the surface normally determined by the surface plasma wave dispersion relation for the described optical structure. Since the surface plasma waves induced by the fluorescent label have no preferred propagation direction along the surface, the induced emission emerges as a cone of radiation in the substrate. Further increase in the intensity of induced emission detected is achieved by employing 360° azimuthal collection to capture the entire cone. The detected signal is then analyzed to determine the ligand concentration. The signal-to-noise ratio is further improved by excluding collection of the light in the plane of incidence, thereby minimizing background signal due to the incident and reflected light.

DETAILED DESCRIPTION OF THE INVENTION

Figure 1:
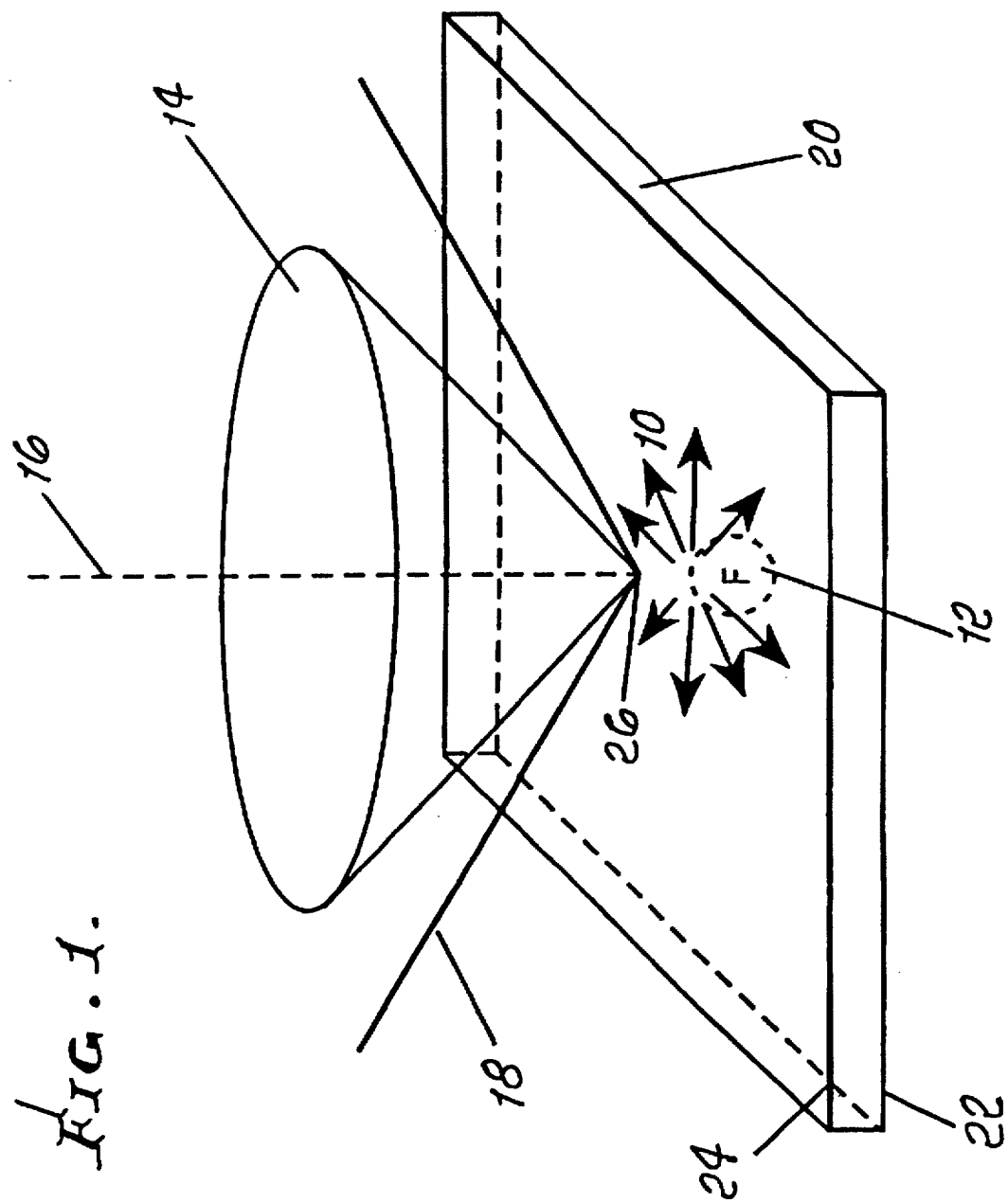
FIG. 1 schematically depicts the arrangement of an optical system for generating surface plasmon resonance fluorescence.

A surface plasma wave, commonly referred to as a surface plasmon, is a longitudinal oscillation (compression wave) in the conduction band electrons near the surface of a metal, semiconductor, or other conducting medium. Surface plasma waves are sensitive to changes in the optical properties of media near the surface along which they propagate. As such, they are useful probes for detecting near-surface phenomena, molecular binding to surface adsorbed molecules being one example. For surface plasma waves to serve in such a capacity, however, one must employ (1) a technique for exciting the surface plasma waves, and (2) a method for detecting changes induced by the surface phenomenon of interest in the properties of the surface plasma waves.

One common technique for exciting surface plasmon waves is attenuated total reflection (ATR) coupling. In this technique, a portion of the energy from a beam of light is converted into surface plasma waves via a stratified optical system that, in its simplest form, consists of three components:

(a) Substrate: This layer functions as an internal reflection element (IRE) for the excitation light. As such, it must be transparent to the excitation light.

(b) Film: This is the layer within which the propagation of surface plasmon waves is to be supported. It is thin (~100–1000 angstroms) compared to the other layers and is not necessarily homogeneous.

(c) Sample: The surface phenomenon being detected occurs within this medium near its boundary with the film. In order for the substrate to function as an internal reflection element, the substrate must have a higher index of refraction than the sample.

In some applications, the order of the film and the sample may be reversed.

Equally as important as the material structure of the system is the nature of the excitation beam. To excite surface plasma waves, the beam must fulfill a minimum set of criteria:

(a) Polarization: The beam must have a component that is p-polarized with respect to the substrate/film interface.

(b) Wavelength: The wavelength must be greater than a certain minimum value determined by the plasma frequency of the film.

(c) Angle of incidence: The beam must be incident on the substrate/film interface at an angle whose value falls within a range of angles determined by the thickness and dielectric coefficients of the layer media, and the wavelength of the beam.

With regard to the last criterion, all excitation angles, as referenced to the normal of the surface defined by the substrate/film interface, are greater than the critical angle for total internal reflection between the substrate and sample media. Among these angles there are two of note. The attenuated total reflection minimum is the angle at which the internally reflected beam undergoes a dramatic reduction in intensity due to energy absorption and dissipation (in the form of Joule heating) by the induced surface plasmon waves, and destructive interference effects at the substrate/film interface. The interfacial enhancement maximum is the angle at which the surface plasmon wave associated electromagnetic field in the sample layer acquires a maximum intensity. For some films, these two angles are so close as to be almost indistinguishable, e.g., silver. In others, the difference is quite pronounced, e.g., iron (Olney, R. D. and Romagnoli, R. J., Applied Optics 26:2279 (1987)).

A system arranged according to the above description can generate surface plasma waves along the film/sample interface. This phenomenon is referred to as surface plasmon resonance (SPR). Since a surface plasma wave is made up of moving charges, there is associated with it an electromagnetic wave that propagates along the same direction. The field intensity of the electromagnetic wave diminishes exponentially with distance from the film/sample interface. Such a wave is called an evanescent wave and the electromagnetic field associated with it is referred to as an evanescent field. The extent of the evanescent field can be characterized by the penetration depth, defined as the distance at which the field strength decays to 1/e, or 37%, of its value at the film/sample interface. Its value is typically only a fraction of the excitation wavelength. As an example, for $\lambda=600$ nm one obtains for silver and gold penetration depths of 390 and 280 nm, respectively (Raether, H., Surface Plasmons on Smooth and Rough Surfaces and on Gratings, Springer Tracts in Modern Physics, Vol. III, pg 6 (Springer Verlag, New York 1988)). It is the evanescent field that is responsible for the sensitivity of surface plasma waves to changes in optical properties near the film/sample interface. The frequency of the evanescent wave is that of the surface plasma wave which is, in turn, that of the excitation beam. It is therefore possible to excite fluorescent molecules within the evanescent field near the film/sample interface if the frequency of the excitation beam is an absorption frequency of the fluorophore. Fluorescent molecules in the region beyond the evanescent field are not excited.

All of the interactions discussed thus far are reciprocal in nature. As a result, the excited fluorescent molecules emit an evanescent wave which generates a new set of surface plasma waves oscillating at the fluorophore emission frequency. These surface plasma waves then radiate propagating waves of the same frequency through the film and into the substrate material where they emerge at an angle determined by the surface plasma wave dispersion relation of the system (Benner, R. E. et al, Optics Communications, 30:145 (1979)). Detection of the intensity of the induced emission gives a relative measurement of the surface density of fluorescent molecules. Since the amplitude of the evanescent field exceeds that of the incident field by a factor of 10 to 100 times depending on the materials used for the stratified optical system, the evanescent field enhances the emission from fluorescently labeled ligand bound to the film surface.

FIG. 1 shows a schematic representation of the induced emission. Since the surface plasma waves 10 (represented by arrows) induced by the fluorescent label 12 adjacent to the film/sample interface surface 22 of the film 20 have no preferred propagation direction along the film/sample interface surface, the induced emission emerges from the substrate/film interface surface 24 of the film as a conical shell of radiation 14 whose axis of symmetry coincides with the substrate/film interface surface normal 16 at the point 26 at which the excitation beam 18 is incident on the film (Weber, W. H. and Eagen, C. F., Optics Letters, 4:236 (1979)).

Conventional approaches described in the prior art for capturing the induced emission confine collection to one azimuthal angle at a fixed distance from the point of origin of the induced emission. Thus collection is along only one dimension in a spherical coordinate system.

According to the present invention, the induced emission signal is increased and assay performance is improved by providing the means to capture the entire induced emission cone by choosing substrate geometries that allow collection along two angular dimensions in a spherical coordinate space.

In its broadest embodiment, the present invention is concerned with improvements in the method of light collection for the induced emission of surface plasmon resonance based sensing devices which involve (a) Irradiating the film of the stratified optical system from the substrate side with light that has a wavelength, polarization and angle of incidence appropriate for exciting surface plasmon resonance fluorescence;

(b) Incubating the sample containing fluorescent or fluorescently labeled molecules in contact with the film, where said film may or may not be chemically modified; and (c) Employing 360° azimuthal collection of the fluorescence induced emission cone, and analyzing the rate or amount by which the detected induced emission signal changes as binding between the fluorescent or fluorescently labeled molecules and the film progresses.

The stratified optical system comprises a substrate, sample, and one or more layers of material collectively referred to as "film" interposed therebetween. It required that one of the layers of which the film is comprised be a conductor, such as silver or gold, with thickness in the range of approximately 10 nm to 100 nm. It is this layer that supports the propagation of the various modes of surface plasma waves. Additional layers are optional. Those interposed between the substrate and the conductor layer are hereinafter called "underlayers". Those interposed between the conductor layer and the sample are hereinafter called "overlayers". Both underlayers and overlayers are usually dielectric materials such as LiF, $MgF_2$, and $SiO_2$, with thickness ranging from 2 nm to 1500 nm, depending on the application. For example, a thin layer of chromium oxide (3–5 nm thick), may be used as an underlayer to increase adhesion between a conductor layer of gold (50 nm thick) and a BK-7 glass substrate. Deposition of each layer on the substrate can be done by thin-film coating techniques which include physical vapor deposition and chemical vapor deposition. Such techniques are well known in the art.

The substrate functions as an internal reflection element (IRE) for the excitation light. As such, it must be transparent to the excitation light. Glass, silica, and optical plastics such as polystyrene, polycarbonate, acrylic, polymethylpentene, and their copolymers are examples of commonly used substrate materials that are transparent to visible light. The fundamental geometry of the substrate is determined by the requirement that it be conducive to maximal collection of the induced emission cone. According to the present invention, the preferred substrate material is some type of optical plastic and the preferred process for fabricating the substrate in a particular geometry is injection molding. The advantages of using molded plastics are that of low cost and the capability of molding additional features into the substrate for indexing the substrate with an instrument.

In another embodiment of the invention, the geometry of the substrate surface includes a 360° surface of revolution with axis of symmetry normal to the substrate/film interface.

In other embodiments, the assay is an indirect ligand labeled analyte/fluorescent labeled anti-ligand competitive assay.

Yet a further embodiment is based on a two step saturation assay.

Figure 2:
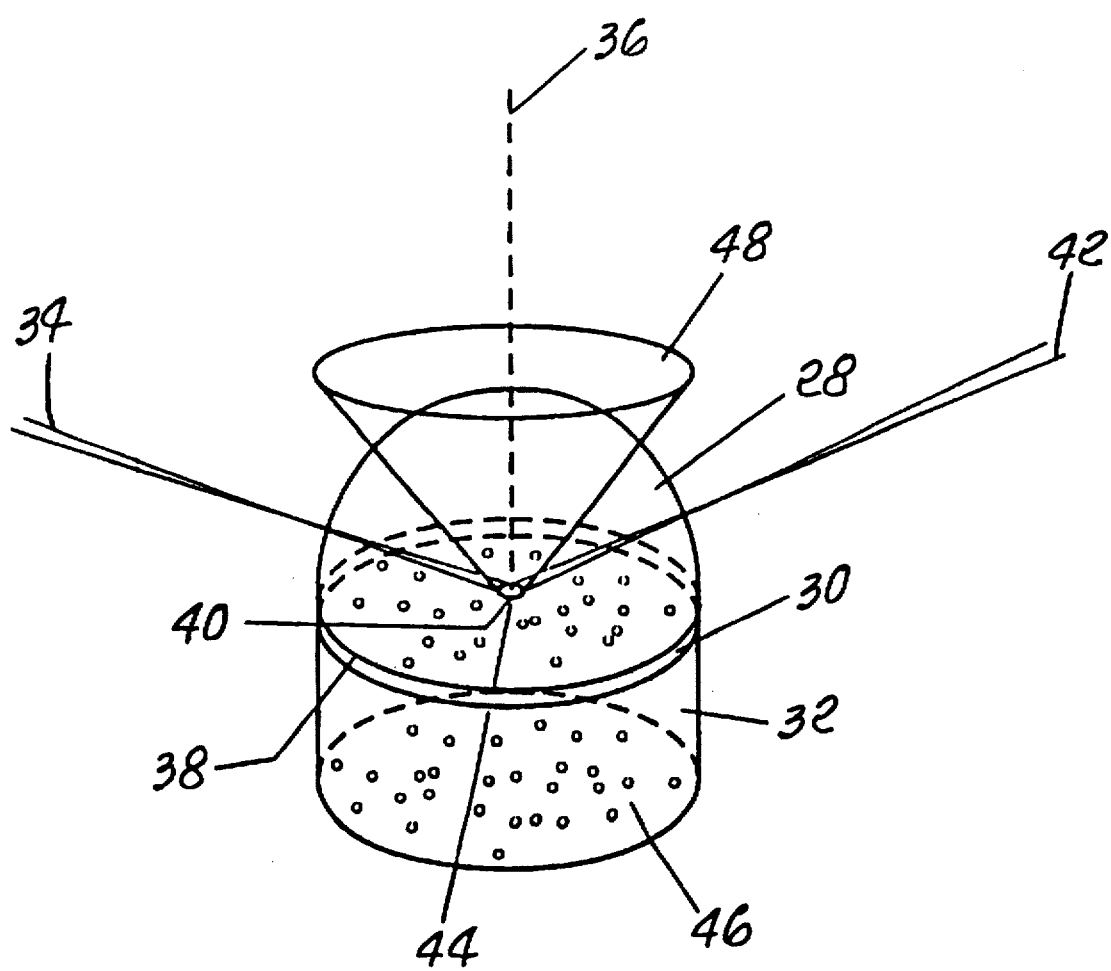
FIG. 2 schematically depicts the arrangement of an optical system for generating surface plasmon resonance fluorescence to detect fluorescent molecules binding at a liquid/solid-phase interface by utilizing a substrate geometry that includes a surface of revolution (hemisphere).

Hereinafter, the term "surface of revolution" will refer to any surface whose union with a plane perpendicular to its axis of symmetry forms a circle. There are many examples of geometric solids with such surfaces, including a hemisphere, ellipsoid, cone, and paraboloid. In FIG. 2, a hemispherical substrate 28 coated with a thin conducting film 30 which supports surface plasmon waves is in contact with the sample 32. The excitation light 34 irradiates the spherical surface at an angle or range of angles appropriate to the excitation of surface plasmon resonance. These angles are referenced to the axis of symmetry 36 of the substrate which is also a normal line of the plane defined by the substrate/film interface 38. The light continues to propagate through the substrate medium and undergoes attenuated total reflection at the center 40 of the substrate/film interface. The excitation light propagating inside the substrate is either collimated, converged, or diverged by a predetermined amount to accommodate angular variation of the orientation of the substrate within its alignment tolerance. The reflected light 42 emerges from the other side of the substrate. The fluorescent molecules 44 within the penetration depth of the evanescent field of the induced surface plasma waves are excited, whereas the fluorescent molecules 46 beyond the penetration depth, i.e., those in bulk solution, are not. The half-angle of the induced emission cone 48 has a longer wavelength than the excitation light and, therefore, is always less than the excitation angle of incidence due to dispersion effects within the substrate material. The primary advantage of using a hemispherical substrate is that the general character of the induced emission cone remains intact when it emerges from the substrate. This facilitates collection of the induced emission to a substantially improved degree as compared with prisms, such as right triangular and hemicylindrical prisms, which have geometries incompatible with the induced emission cone as well as sharp corners that scatter light.

Figure 3:
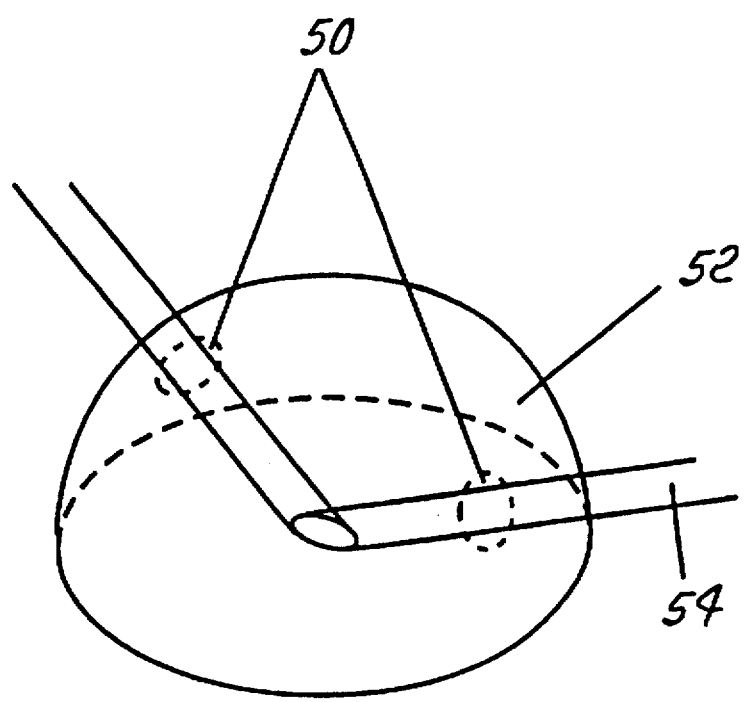
FIG. 3 shows the use of flat windows on a surface of revolution substrate for entry/exit of the excitation beam into/out of the substrate medium.

In a further embodiment, the present invention provides a means for reducing the background which, in turn, improves the signal-to-noise ratio. This is accomplished by minimizing divergence of the Fresnel reflection of the excitation light incident on the surface of the substrate. As shown in FIG. 3, and again using the example of the hemispherical substrate, two flat optical windows 50 are incorporated into the substrate 52 at the entry and exit points of the excitation light 54. The windows are oriented at a predetermined angle with respect to the substrate/film interface. Unlike a curved surface, the flat windows will not change the wavefront curvature of that portion of excitation beam that undergoes Fresnel reflection thereby enabling easier removal of such light from the system. The size of the windows is determined by the size of the excitation beam. As a rule of thumb, the size of the windows should be small and the location of the windows should be such as to cause minimal interference with the radiation cone.

As an added benefit, the presence of flat windows increases system sensitivity to induced emission by enabling better collimation of the excitation light within the substrate medium. Since surface plasma waves will only be excited by light impinging on the substrate/film interface within a relatively small range of incidence angles, an excitation beam that is sufficiently decollimated within the substrate medium will not transfer all of the energy it could potentially contribute to the generation of excitation plasmons. Furthermore, energy that is not used in the generation of plasmons will be reflected from the substrate/film interface and contribute to the background. The combined result of lower induced emission and higher background results in an overall loss of sensitivity. Since all surfaces of revolution are curved, a substrate that includes such a surface will have an optical power that must be corrected for with external optics to ensure internal collimation of the excitation beam. In practice this is difficult to achieve for small substrate sizes within the collimation requirements for surface plasmon resonance fluorescence due to aberration effects generated at the substrate surface. Externally collimated light incident through a flat window at the substrate surface eliminates the need for such correction.

Figure 4:
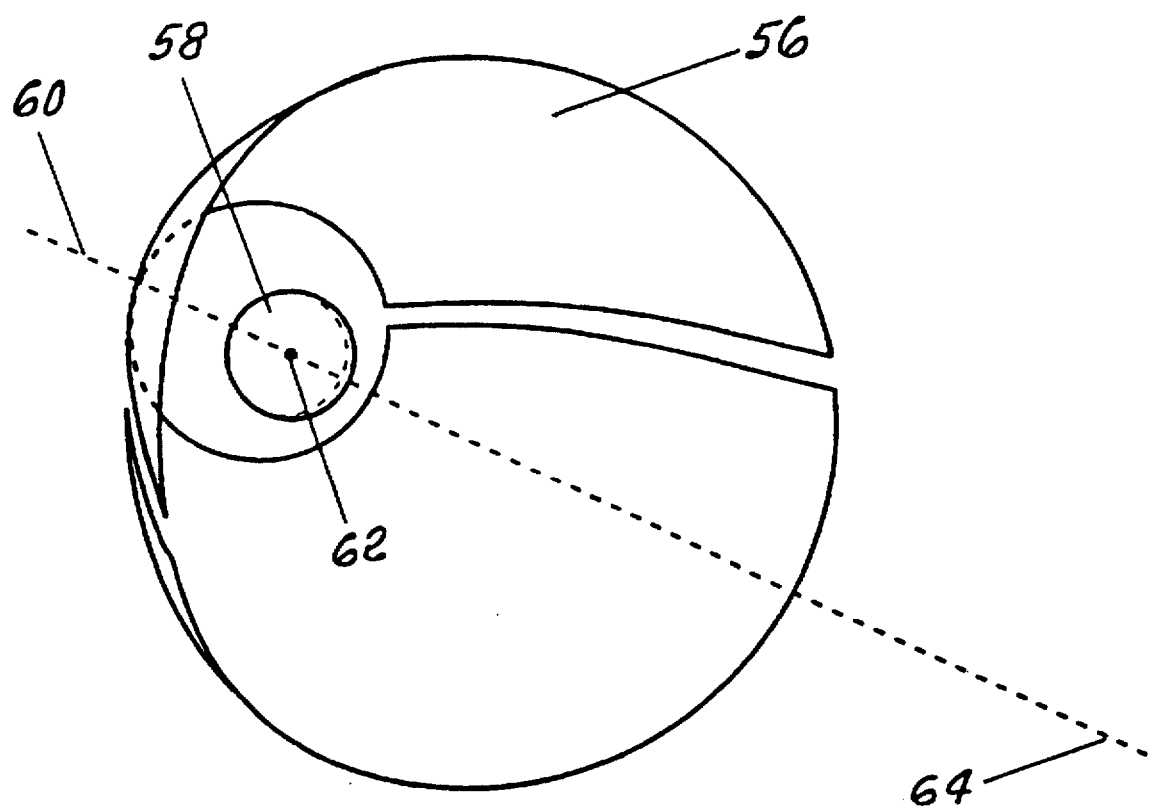
FIG. 4 illustrates the arrangement of a conic-section reflector, with slots for entry/exit of the excitation beam into/out of a surface of revolution sensor, for near 360° collection of the induced emission.

For commonly used substrate materials (index of refraction of approximately 1.5–1.6) the half-angle of the induced emission cone is often relatively large (greater than 65°) making collection by refraction techniques, (e.g. lensing) difficult. The use of reflection techniques (e.g., employing mirrors or internal reflection elements) provides a more practical solution, particularly if the reflecting surface shares the rotational symmetry of the radiation cone. The most significant example is the use of conic section surface reflectors (e.g., paraboloidal and ellipsoidal surface reflectors) for redirecting widely divergent light radiated from a point source along a clearly defined optical axis. Since the radiation cone can be thought of as originating at an approximate point source located at its apex, it lends itself well to such collection techniques. As an example, FIG. 4 shows an ellipsoidal surface reflector 56. The hemispherical substrate 58 is positioned in such a way that (1) its axis of symmetry is coincident with the axis of symmetry of the reflector 60, (2) its center of curvature (where the incident light irradiates the film to excite surface plasmon resonance fluorescence) is coincident with internal focus 62 of the reflector, and (3) its hemispherical side is facing toward the external focus 64 of the reflector. The ellipsoidal reflector reflects the radiation cone emanating from the center of curvature to the external focus where a light detection device is located. Techniques for designing such an optical system using reflectors for maximal light collection, and techniques for fabricating the required optical components are well known in the field of optics (Wilford, W. T. and Winston, R., High Collection Noniniaging Optics, (Academic Press Inc., NY. N.Y., pp 53–97, 1989)).

Figure 5:
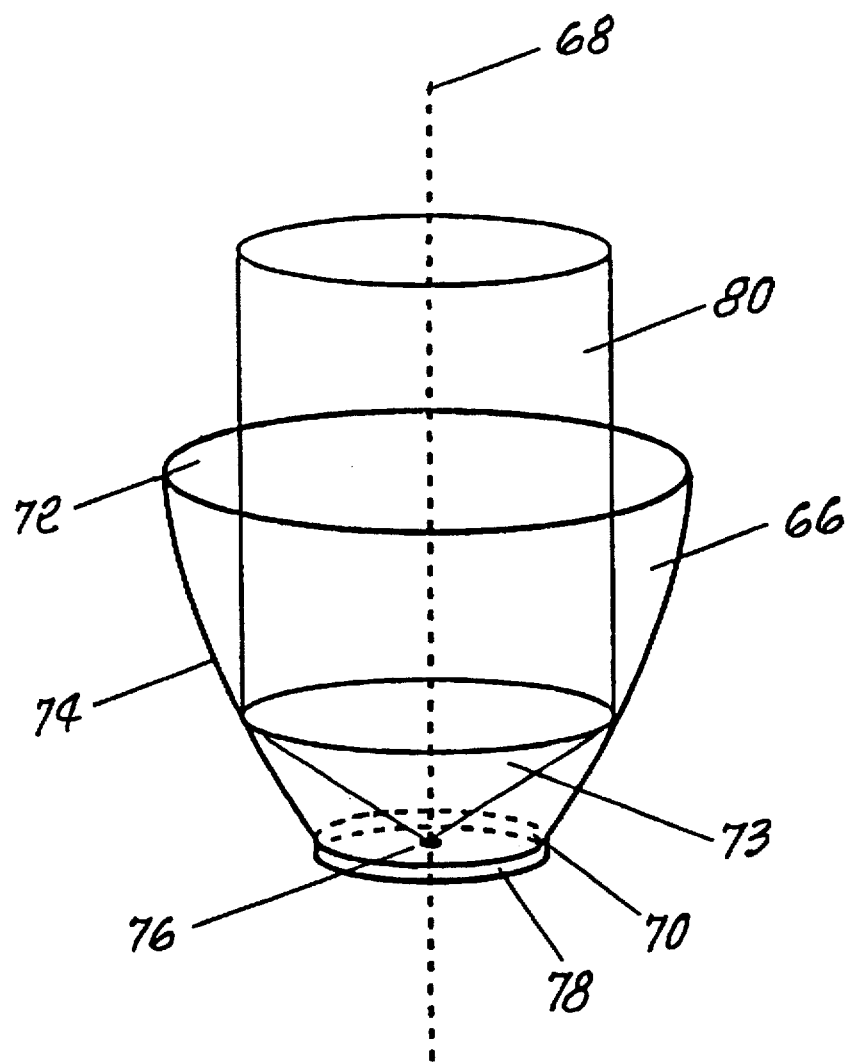
FIG. 5 shows the use of a sensor with a surface of revolution substrate (truncated plano-paraboloid) that employs total internal reflection for 360° collection of the induced emission.

In another embodiment of the present invention, one surface of the substrate is a 360° surface of revolution with axis of symmetry normal to the substrate/film interface at the point at which the excitation light is incident that functions as an internal surface reflector for the radiation cone. One example is the truncated plano-paraboloidal substrate 66 shown in FIG. 5. The substrate shape is obtained by slicing a paraboloid along two planes to which the paraboloidal axis of symmetry 68 is normal; the emergence plane 70 contains the focus of the paraboloid and the exit plane 72 is any plane farther from the focus than the plane in which the cone 73 intersects the paraboloidal surface 74 when (1) they share the same axis of symmetry 68, (2) the cone apex and paraboloid focus 76 coincide, and (3) both the cone and the paraboloid open in the same direction. The section of the paraboloid between these two planes defines the shape of the substrate. The device is completed by coating the film 78 onto the planar surface of smaller diameter, i.e. the emergence plane. The stratified optical system is utilized by bringing a fluorescent material into contact with the film and guiding the excitation beam (by using windows, for example) into the substrate in such a way that it is incident on the substrate/film interface at the paraboloidal focus with an angle, wavelength, and polarization appropriate to exciting surface plasmon resonance fluorescence. The resulting radiation cone will be internally reflected from the paraboloidal surface and directed through the larger planar surface where it will emerge as an approximate cylindrical shell 80. Such a radiation pattern can be easily focused onto a detector with a single lens.

In a further embodiment, the present invention provides improved assay techniques for qualitative and/or quantitative detection of chemical or biochemical analytes in a sample and a means for applying such techniques. The types of analytical measurements which can be performed with the present invention are numerous and are obvious to those skilled in the art. However, a few examples will be given by way of illustration only. In one aspect, the invention provides a method for measuring for a ligand in a sample which generally comprises:

(a) Irradiating the film of the stratified optical element from the substrate side with light that has a wavelength, polarization and angle of incidence appropriate for exciting surface plasmon resonance fluorescence;

(b) Incubating the sample which contains ligand and appropriate fluorophore labeled molecules as the tracer (hereinafter called "fluorescently labeled conjugate") in contact with the specific binding partner for the ligand which is coated to the surface of the film which is coated on the substrate; and (c) Employing 360° azimuthal collection of the fluorescence induced emission cone and monitoring and analyzing the rate or amount by which the detected induced emission intensity changes as binding between the fluorescently labeled molecules and the immobilized specific binding partner progresses via direct or bridging binding interactions.

One example of this technique is the "sandwich" immunometric assay technique, also termed the "labeled reagent" technique, in which the assayed ligands have more than one binding site, or epitope, for antibodies. The specific binding partner is immobilized on the surface of the film by physical adsorption or chemical coupling to create either a continuous layer (i.e. monolayer) or discontinuous layer (i.e. island or specific pattern). The solid phase immobilization techniques are well known in the art. As a rule of thumb, the strategy for immobilization is to maintain the maximal activity and accessibility of the immobilized specific binding partner. In a typical one-step sandwich assay (or simultaneous assay) ligand is co-incubated with the fluorescently labeled conjugate (which is present in excess with respect to the ligand) for a predetermined period of time in an appropriate diluent to form ligand/conjugate complexes via affinity interactions prior to being brought into contact with the immobilized specific binding partner. The ligand/conjugate complexes are then immuno-extracted to the solid phase by allowing the ligand portion to bind to the specific binding partner with its remaining epitopes. The induced emission produced by the fluorophore labeled conjugate within the evanescent field of the surface plasma waves emerges from the substrate/film interface into the substrate medium as a conical shell of radiation which is collected by the optical systems heretofore described. Since only the fluorescently labeled conjugates within the evanescent field of the surface plasma waves are excited, the induced emission will increase as more ligand/conjugate complexes diffuse into the evanescent field and are bound there by the specific binding partner. In this way the free and bound ligand and conjugate are separated optically; consequently, there is no need for a washing step to separate the free from the bound analyte. The concentration of the ligand is determined using either an equilibrium mode where the change in absolute intensity is measured, or a kinetic mode where the rate of change in intensity is measured. The rate measurement measures the diffusion of the complexes near the film/sample interface and offers a turn-around-time considerably faster than that of the equilibrium measurement.

The present invention also applies to two-step sandwich assays (or sequential assays) in which the ligand is incubated first with the specific binding partner followed by another incubation with the fluorescently labeled conjugate. In this case a washing step between the two incubations is used. Allergy assays (i.e. specific IgE for allergens) are representative of this category.

Another assay type is the "competitive" assay, also termed the "labeled analyte" technique, in which there exists a competition of the unlabelled ligand (or sample ligand) and the fluorescent labeled ligand for a limited amount of binding sites on the specific binding partner. Like the sandwich assays, the competitive assay can be performed simultaneously or sequentially. Data acquisition and analysis can be done in either the equilibrium or kinetic mode.

Examples of fluorophores which are suitable for use as labels are many and well known in the art. Commonly used fluorescent dyes include rhodamine isothiocyanate, Cy5™, 3, 3-Trimethylindolenium-5-sulfonate pentamethine cyanine-1-(6-pentyl-N-hydroxysuccinimide) ester, available under the Cy⁵ trademark from Amersham Life Sciences, Arlington Heights, Ill.; fluorescein isothiocyanate, allophycocyanin, R-phycoerythrin, B-phycoerythrin, and near IR dyes. Other fluorophores are known to those skilled in the art.

EXAMPLE 1

Observation of Fluorescence Induced Plasmon Emission Cone Using a Hemispherical Substrate (i) Fabrication of Film-coated Substrate A 1/16 inch thick, 1 inch square glass plate was cleaned with aqua regia and rinsed, first with deionized water and then with ethanol. One side of the plate was coated with a 500 angstrom thick layer of gold by vacuum deposition. A 1 inch diameter glass hemisphere was modified by optically grinding and polishing its planar surface to uniformly remove 1/16 inch of material. The uncoated side of the glass plate was then optically coupled to the planar surface of the hemisphere using index matching fluid with refractive index approximately equal to that of the glass. This arrangement resulted in the center of curvature of the hemisphere being approximately located in the plane defined by the interface between the glass plate and the gold layer (the thickness of the layer of index matching fluid was assumed to be negligible).

(ii) Fabrication of Flow Cell

A gasket was made by cutting an elliptical hole in the center of a 1 inch square sheet of silicon rubber. Two holes were drilled in a metal plate and metal tubing was pressed into the holes so that one end of both tubes was flush with one side of the metal plate. The spacing between the holes was chosen to be approximately equal to the distance between the two foci of the ellipse describing the hole in the gasket. The diameter of the metal tubing was appropriate to accommodating the attachment of polyethylene tubing with an inner diameter of 0.040 inches. A mechanical device appropriate for compressing the gasket between the gold coated surface of the glass plate and the side of the metal plate with which both metal tubes were flush was used. Care was taken to ensure the two holes in the metal plate were within the elliptical perimeter of the hole in the gasket when it was compressed.

(iii) Detection System Arrangement

An apparatus was built that enabled the entry aperture of a fiber optic bundle to be positioned anywhere along a hemispherical surface in such a way that the entry aperture was always normally oriented toward the center (hereinafter referred to as the "center of motion" of the entry aperture) of said hemispherical surface. The exit aperture of the fiber optic bundle was attached to a photomultiplier tube (PMT) detection system equipped with a monochromator.

(iv) Experimental Arrangement

The film/substrate and flow cell assembly was placed in such a way that the position of the center of curvature of the glass hemisphere and the position of the center of motion of the entry aperture coincided. The distance between the entry aperture and its center of motion was fixed at a distance of approximately 3 inches. The entry aperture diameter was reduced to 2 mm to improve angular resolution.

A red helium-neon laser (wavelength=632.8 nm), equipped with a 3 nm spectral bandpass laser line filter, was directed at the glass/gold interface along a line radial with respect to the center of curvature of the glass hemisphere and at an angle appropriate to exciting SPRF in the sample used. Suitable optics were inserted between the laser and the sensor to ensure near-collimation of the laser light within the glass material of the optical structure.

(v) Experimental Procedure

A sample solution was made up using an appropriate concentration of a suitable protein labeled with the trimer form of allophycocyanin (hereinafter referred to as "APC). The sample was taken up in a syringe. The syringe was inserted into the free end of one of the lengths of polyethylene tubing on the flow cell device. The free end of the other length of polyethylene tubing was placed in a waste container. The sample was injected into the flow cell until a small amount of it emptied into the waste container. The resulting fluorescence induced emission was visually observed (through a pair of protective laser goggles that block red helium-neon laser light but allow all other visible wavelengths through) by looking down a line of sight radial to the center of curvature of the glass hemisphere at an angle appropriate to the expected radiation cone emission. A sufficient period of time was allowed for complete adsorption of the labeled proteins. Quantitative data was then taken by moving the entry aperture to a particular angular position and using the detection system to obtain a wavelength profile of the collected light (hereinafter referred to as an "emission scan"). Angular position was specified in conventional spherical coordinates; the polar angle (theta) was referenced from the normal line to the glass/gold interface and the azimuthal angle (phi) was referenced from the line defined by the intersection of the plane of incidence and the plane of the glass/gold interface on the laser side of the center of motion. Emission scans were taken at a number of angular positions. The laser light was blocked from striking the substrate between emission scans to lessen photobleaching of the fluorescent molecules labeling the adsorbed proteins.

(vi) Results: Qualitative Observation

The fluorescence induced plasmon emission was immediately visible upon injection of the sample. Varying the polar angle of the line of sight at fixed azimuthal angle resulted in an observed flash of emission light as the polar angle corresponding with the emission angle was crossed. Fixing the polar angle of the line of sight at the emission angle and varying the azimuthal angle yielded an observation that the emission light was visible and appeared uniform in intensity at all positions in the 360° surrounding the sensor. The apparent discreetness along the polar direction and uniformity along the azimuthal direction was taken as qualitative confirmation of the conical shell radiation pattern.

(vii) Results: Quantitative Observation

Figure 6:
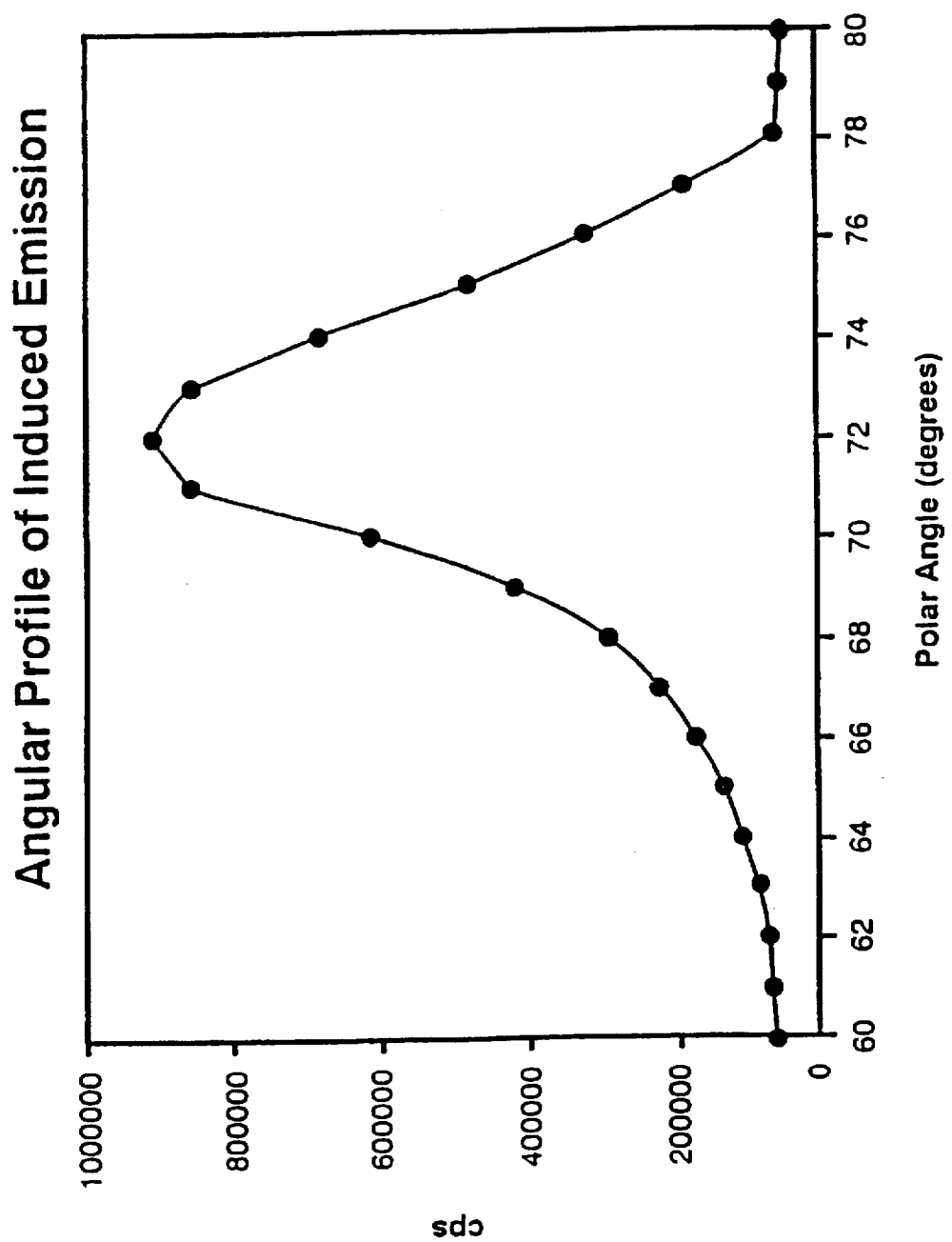
FIG. 6 is a plot of the induced emission intensity as a function of the polar angle as referenced from the substrate side of the axis of symmetry of a hemispherical sensor.

FIG. 6 shows the total number of photons collected at an azimuthal angle of 90° to the incident beam in a 640–700 nm band as a function of polar angle for an angular range of 60° to 80°. Notice the emission angle peak at 72°.

Figure 7:
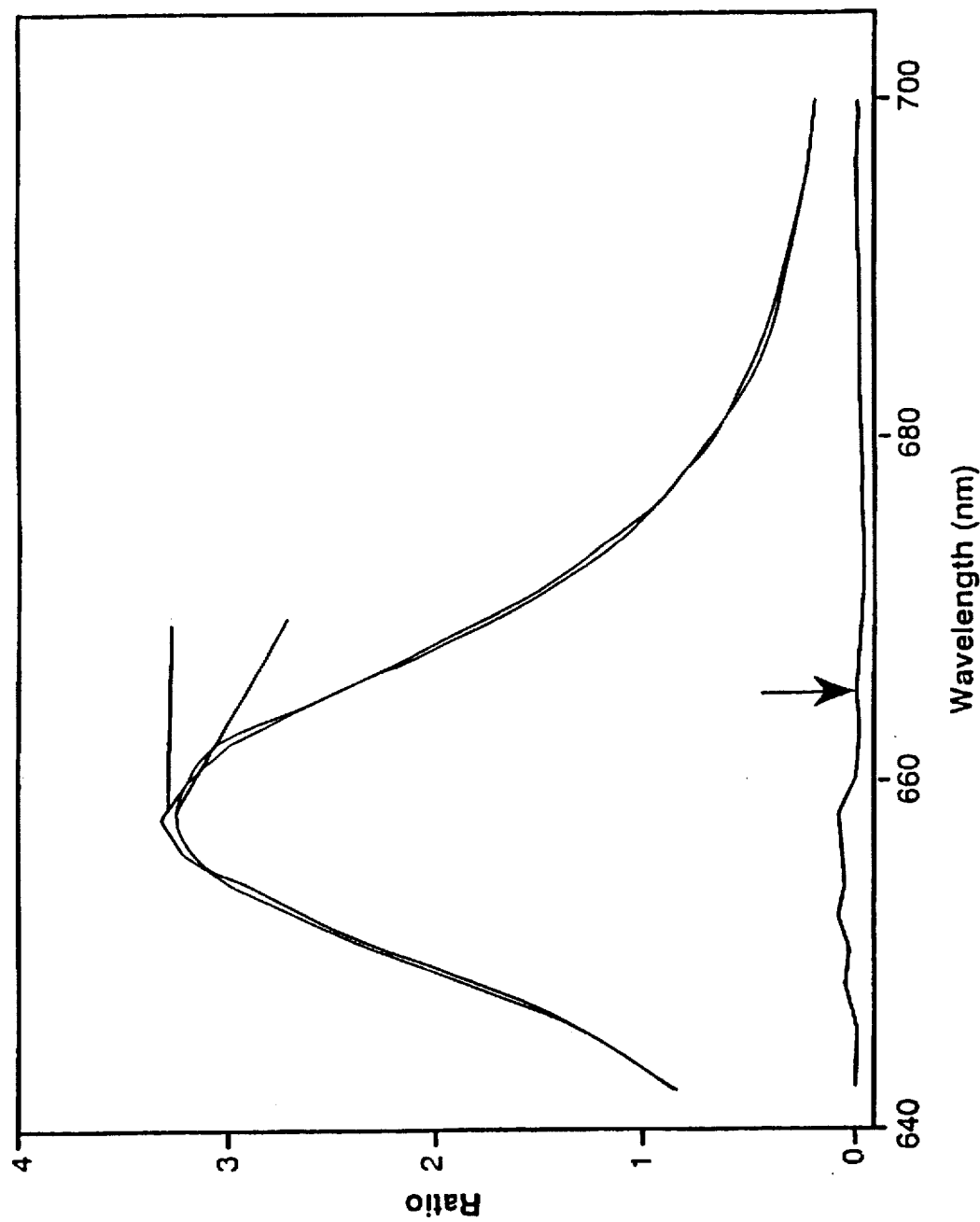
FIG. 7 is a plot comparing the induced emission intensity as a function of wavelength at 90° azimuthal angle to that at 45° azimuthal angle, where the azimuthal angle is referenced counter-clockwise from the projection of the path of the incoming excitation beam onto the substrate/film interface plane when looking from the substrate side.

FIG. 7 shows only those emission scans taken at a polar angle of 72° for two azimuthal angles: 45° and 90°. The comparable profiles of these curves makes evident the uniformity of the emission intensity in the azimuthal direction.

Theoretical calculations using Fresnel's equations for stratified media predict an emission angle of 72.22° for this system. This value compares well with the observed 72° and highlights the usefulness of a hemispherical substrate geometry in maintaining the general character of the fluorescence induced plasmon radiation.

EXAMPLE 2

Surface Plasmon Resonance Fluorescence Assay for Creatine Kinase-MB Using 360° Azimuthal Collection of Fluorescence Induced Plasmon Emission (i) Fabrication of Film/Substrate Structure A hemispherical substrate was molded from optical grade NAS plastic. The planar surface of the hemisphere was coated with a 470 angstrom thick layer of gold.

(ii) Assay Methodology

A sandwich assay was performed on spiked solutions of CK-MB in bovine serum. Capture antibodies were immobilized on the gold surface of the sensor using biotin-streptavidin chemistry. Each of the premixed solutions was allowed to incubate with a conjugate solution containing a 150 nM concentration of APC labeled antibody for 2 minutes prior to being brought in contact with the gold surface.

(iii) Experimental Arrangement

Figure 8:
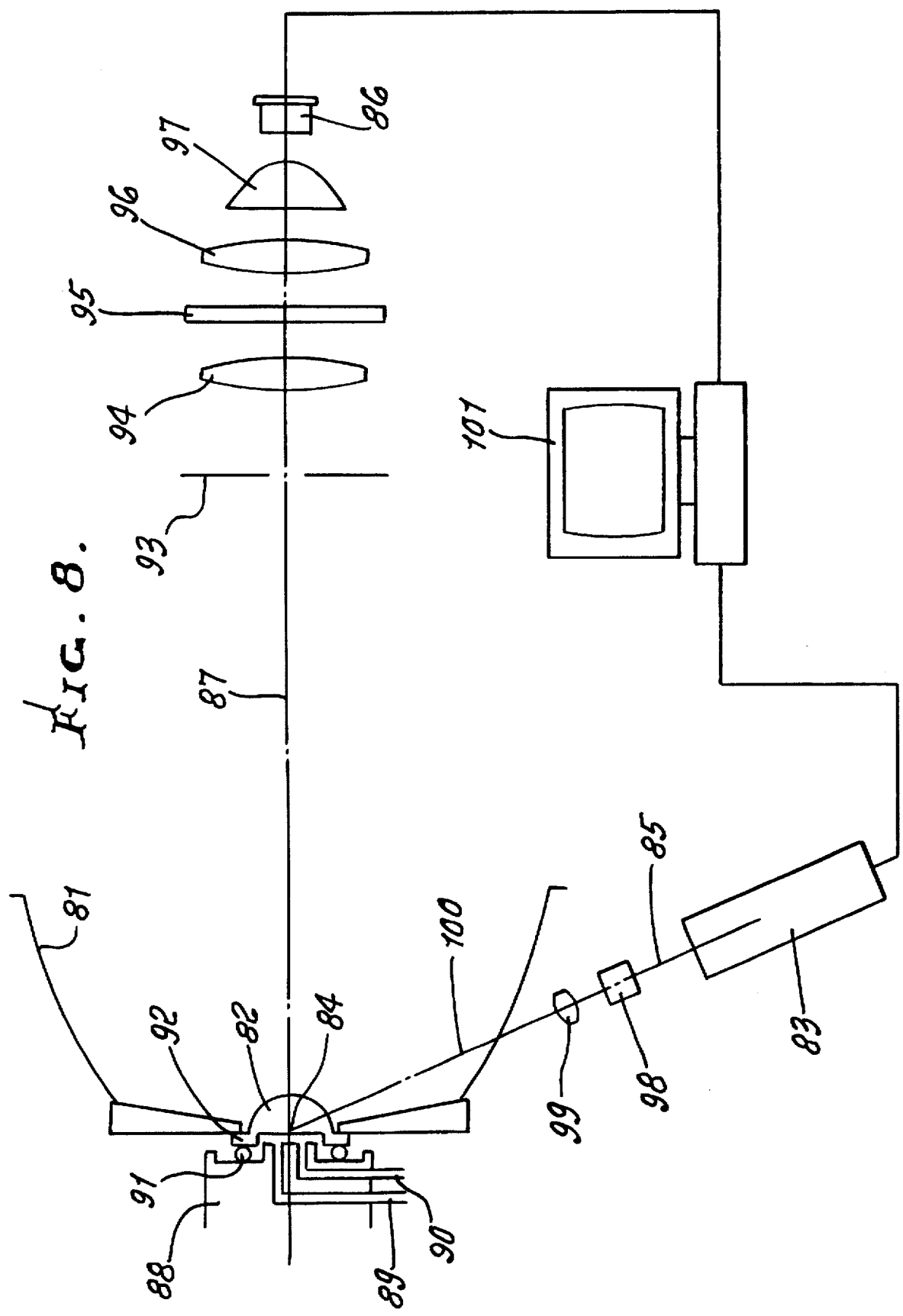
FIG. 8 represents schematically (top view) an apparatus of one embodiment of the invention for measuring the optical changes of the fluorescent induced emission involved in Example 2.

In FIG. 8, an ellipsoidal surface reflector 81 with a focus to focus length 20 times the diameter of the hemispherical substrate 82 was cut along a sagittal plane containing its major axis 87 to produce two slots (as shown more clearly in FIG. 4). The width of the slots was such that each subtended an angle of 9° at the internal focus 84 of the reflector in a plane perpendicular to the major axis. A red diode laser 83 (wavelength=635 nm), meant to function as the excitation source, was mounted on an armature that allowed the laser to shine through one of the slots and to be rotated about the internal focus of the reflector in such a way that the beam 85 was always directed at the internal focus. A photon detector 86 was positioned in front of the reflector along its axis of symmetry 87. The antibody-coated hemispherical substrate was mounted in a flow cell device 88 consisting of an inlet 89, an outlet 90, and an O-ring 91 like that described in Example 1. The hemispherical substrate was then positioned in such a way that (1) its axis of symmetry was coincident with the axis of symmetry of the reflector, (2) its center of curvature was coincident with the internal focus of the reflector, and (3) its hemispherical side was facing toward the external focus of the reflector. Positioning of the substrate in this way allowed the laser beam to be reflected from the center of the substrate/gold interface 92 and out of the remaining slot. Appropriate optics consisting of a polarizing beamsplitter 98 and a collimating lens 99 were inserted between the laser and the outer surface of the reflector to ensure near-collimating within the substrate. Appropriate optics consisting of an adjustable iris 93, a collimating lens 94, an emission filter 95, a focusing lens 96, and a condenser 97 were inserted between the ellipsoidal reflector and the detector for guiding the fluorescence induced emission cone 100 onto the detector. Excitation and emission filters appropriate to the excitation spectrum/fluorophore combination being used were inserted in front of the laser and detector, respectively. Laser and detector were connected to a desk-top computer 101 for power, control, and data acquisition.

(iv) Experimental Procedure

Phosphate buffered saline solution (hereinafter referred to as "PBS") was injected into the flow cell and the position of the laser was adjusted to the angular position of the attenuated total reflection minimum as indicated by a sharp decrease in the intensity of the reflected beam. The integration time of the detector was set at I s. The steps that follow were repeated for solutions with concentrations of 0.00, 1.95, 3.90, 15.6, 62.5, 250, and 500 ng/mL of CK-MB in bovine serum. The CK-MB solution was spiked into the APC-antibody conjugate solution with 1:5 dilution and allowed to incubate for 2 minutes prior to injection. Data collection was initiated 30 seconds prior to injection to obtain a background reading. The sample was allowed to incubate in the flow cell for 60 seconds and then washed with PBS.

(v) Results

Figure 9:
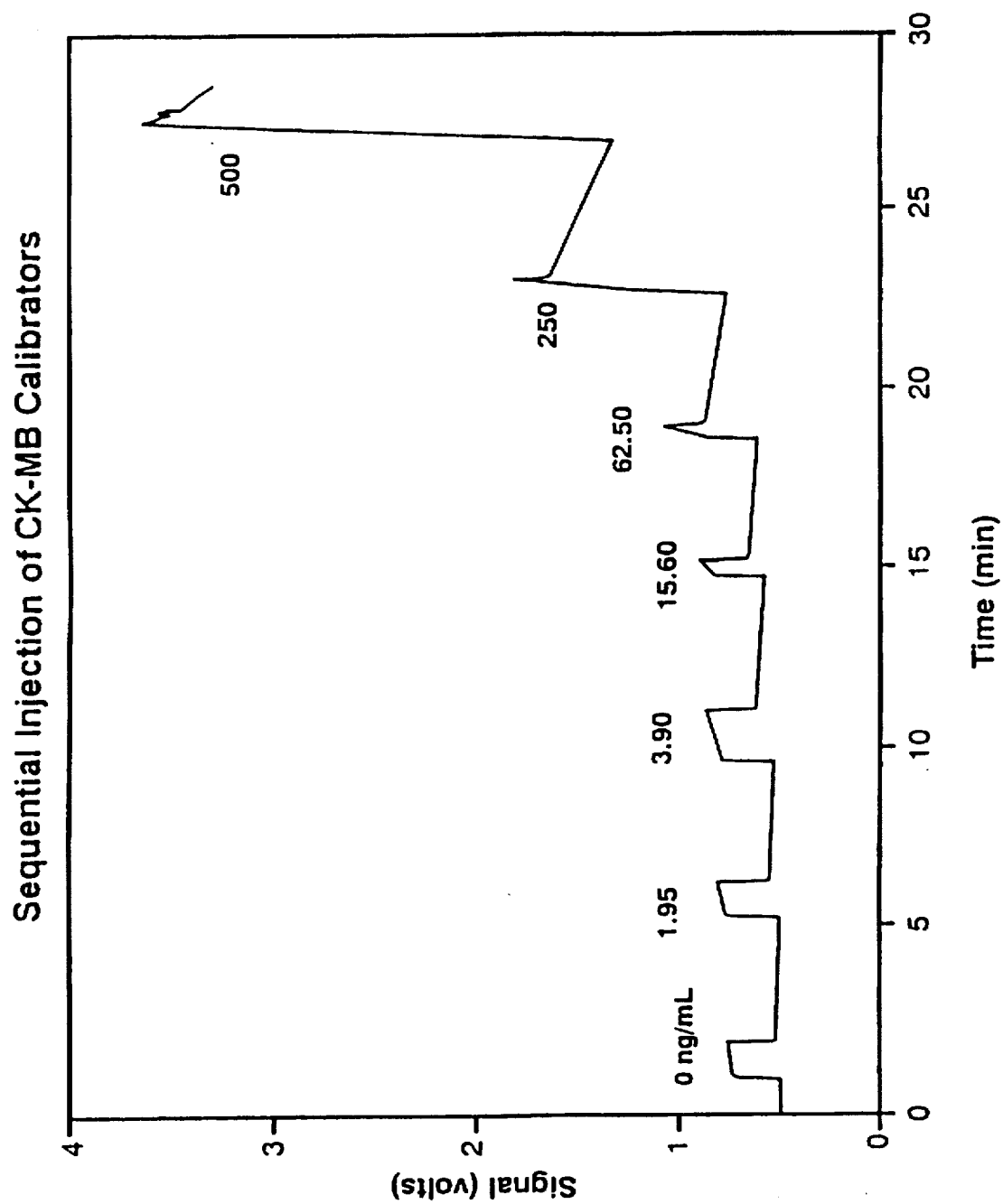
FIG. 9 is a plot of the detector signal due to induced emission from a sensor that was sequentially exposed to seven calibrators of different analyte (CK-(MR)) concentrations.
Figure 10:
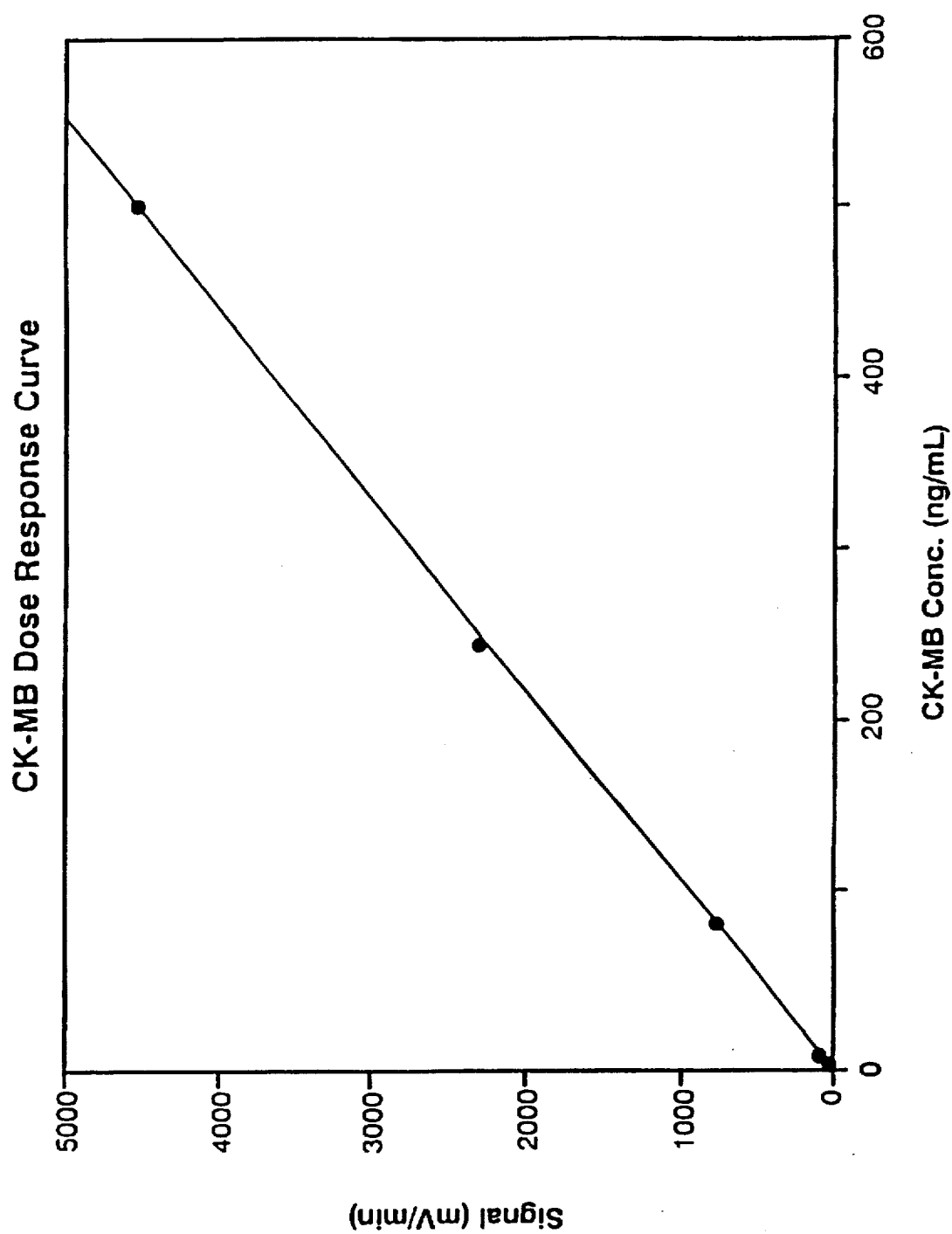
FIG. 10 is the standard curve generated from the induced emission binding slopes in FIG. 9.

FIG. 9 shows the detector signal as a function of time. The domain of each peak is the time between injection and wash of a particular concentration sample. Within each of the time intervals, the detector signal increases in a linear fashion. This is due to the increase in fluorescence induced surface plasmon radiation as the fluorophore labeled analyte accumulates near the gold surface by binding to the capture antibody. Note that the slope of the linear increase rises as the sample concentration of analyte and is thus interpreted as a response to sample concentration. The slope of each concentration point is plotted in FIG. 10 and shows a linear response from 1.95 ng/ml to 500 ng/ml of CK-MB.

The above examples and drawing are intended for illustrative purposes of the invention and are not limiting in scope

We claim:

1. An immunoassay method for determining the presence or amount of an analyte in a body fluid which comprises:
    (a) providing an optical structure comprising in sequence (i) a transparent solid phase substrate coated with (ii) a metal, film which supports surface plasmon resonance, wherein (iii) a first specific binding partner for said analyte is directly or indirectly immobilized on said metal film;
    (b) contacting said first specific binding partner with said body fluid and a tracer comprising a fluorescent label conjugated to either (i) said analyte or an immunological analog thereof or (ii) a second specific binding partner for said analyte;
    (c) irradiating said substrate with excitation radiation of a wavelength, polarization and angle of incidence sufficient to produce said surface plasmon resonance and to induce an emission cone of fluorescence from any specifically bound tracer;
    (d) measuring any change in rate or amount of said fluorescence emission over a predetermined time period using a fluorescence collection means which captures essentially all said fluorescence in said emission cone, said means having a substrate geometry which collects said fluorescence emission along two angular dimensions in a spherical coordinate space; and
    (e) determining the presence or amount of said analyte in said body fluid from said measured change in the rate or the amount of said fluorescence emission.

2. The method according to claim 1 wherein said metal film has a thickness of about 10 nm to about 100 nm.

3. The method according to claim 1 wherein said optical structure further comprises an underlaying dielectric layer interposed between said substrate and said metal film and/or an overlaying dielectric layer interposed between said metal film and said first specific binding partner, each dielectric layer having a thickness of about 2 nm to 1500 nm.

4. The method according to claim 1 wherein said substrate is selected from the group consisting of glass, silica and optical plastic.

5. The method according to claim 1 wherein said substrate is transparent to radiation between 400 nm to 1500 nm.

6. The method according to claim 1 wherein said analyte is selected from the group consisting of an antigen, an antibody, a hapten or an immunoreactive fragment thereof.

7. The method according to claim 6 wherein said antigen is a protein, an enzyme, or an oligonucleotide.

8. The method according to claim 6 wherein said hapten is a hormone, a drug or an allergen.

9. The method according to claim 1 wherein said method is a simultaneous immunometric method and said tracer is said fluorescent-labeled second specific binding partner.

10. The method according to claim 1 wherein said method is a sequential immunometric method and said tracer is said fluorescent-labeled second specific binding partner.

11. The method according to claim 1 wherein said method is a competitive immunoassay and said tracer is said fluorescent-labeled analyte or immunological analog thereof.

12. The method according to claim 11 wherein said fluorescent label is indirectly conjugated to said analyte or immunological analog thereof through a ligand-antiligand bond such that said fluorescent label is bound to said ligand and said analyte or immunological analog thereof is bound to said antiligand.

13. The method according to claim 11 wherein said first specific binding partner is saturated with said tracer prior to contact with said body fluid.

14. The method according to claim 1 wherein said fluorescent label is a fluorescent dye selected from the group consisting of 3,3-trimethylindolenium-5-sulfonate pentamethine cyanine-1-(6-pentyl-N-hydroxysuccinimide) ester, rhodamine isocyanate, fluorescein isocyanate, allophycocyanin, R-phycoerythrin, B-phycoerythrin, or a near infrared dye.

15. The method according to claim 1 wherein said fluorescent label is a dyed fluorescent particle.

16. The method of claim 1 wherein the assay is an indirect ligand labeled analyte/fluorescent labeled anti-ligand competitive assay.

17. The method of claim 1 wherein the method is a two step saturation assay.

18. A method of improved collection of fluorescence emission in a surface plasmon resonance fluorescence immunoassay comprising contacting a body fluid to be tested for an analyte with a stratified optical system, said system comprising in sequence a transparent substrate interfaced with a metal film which supports surface plasmon resonance on which is immobilized a first specific binding partner for said analyte, and a tracer comprising a fluorescent label conjugated to either said analyte, an immunological analog thereof, or a second specific binding partner for said analyte; irradiating said stratified optical system from said substrate side with excitation radiation of a wavelength, polarization and angle of incidence to produce said surface plasmon resonance and to induce an emission cone of fluorescence from specifically bound tracer; measuring any change in rate or amount of said fluorescence emission over a predetermined time; and, correlating said measured change in rate or amount of said fluorescence emission to the presence or amount of said analyte; wherein said improvement comprises measuring said change in rate or amount of said fluorescence emission using a fluorescence collection means which captures essentially all said fluorescence in said emission cone, said means having a substrate geometry which collects said fluorescence emission along two angular dimensions in a spherical coordinate space.

19. The method according to claim 18 wherein said substrate geometry comprises a 360° surface of revolution with an axis of symmetry normal to said interface between said substrate and said film.

20. The method according to claim 19 wherein said surface of revolution is a hemisphere, an ellipsoid, a cone, a paraboloid or a truncated planoparaboloid.

21. The method according to claim 18 wherein said substrate is shaped as a hemisphere, an ellipsoid, a cone, a paraboloid or a truncated planoparaboloid; and wherein said excitation irradiation enters and exits said substrate through a flat optical entrance window and a flat optical exit window, respectively, in order to minimize divergence of Fresnel reflection of said entering excitation irradiation.

22. The method of claim 18 wherein said collection means further comprises paraboloidal or ellipsoidal surface reflectors positioned relative to the substrate to redirect divergent excitation irradiation along a defined optical axis to maximize collection of said fluorescence emission.

23. A surface plasmon resonance apparatus for fluorescence immunoassay of an analyte in a sample, said apparatus comprising:
 (a) an optical structure comprising in sequence (i) a transparent solid phase substrate coated with (ii) a metal film which supports surface plasmon resonance, wherein (iii) a first specific binding partner for said analyte is directly or indirectly immobilized on said metal film, such that a tracer comprising a fluorescent label conjugated to either (1) said analyte or an immunological analog thereof or (2) a second specific binding partner for said analyte is bound to said optical structure in an amount proportional to the amount of said analyte in said sample upon contact between said optical structure, said sample and said tracer;
 (b) a light source positioned to irradiate said optical structure from said substrate side with excitation radiation of a wavelength, polarization and angle of incidence sufficient to produce said surface plasmon resonance and to induce an emission cone of fluorescence from any optical structure bound tracer; and,
 (c) a fluorescence collection means which captures essentially all said fluorescence in said emission cone, said means having a substrate geometry which collects said fluorescence emission along two angular dimensions in a spherical coordinate space.

24. The apparatus according to claim 23 wherein said metal film has a thickness of about 10 nm to 100 nm.

25. The apparatus according to claim 23 wherein said optical structure further comprises an underlaying dielectric layer interposed between said substrate and said metal film and/or an overlaying dielectric layer interposed between said metal film and said first specific binding partner, each dielectric layer having a thickness of about 2 nm to 1500 nm.

26. The apparatus according to claim 23 wherein said substrate is selected from the group consisting of glass, silica and optical plastic.

27. The apparatus according to claim 23 wherein said substrate is transparent to radiation between 400 nm to 1500 nm.

\* \* \* \* \*